Figure 3:
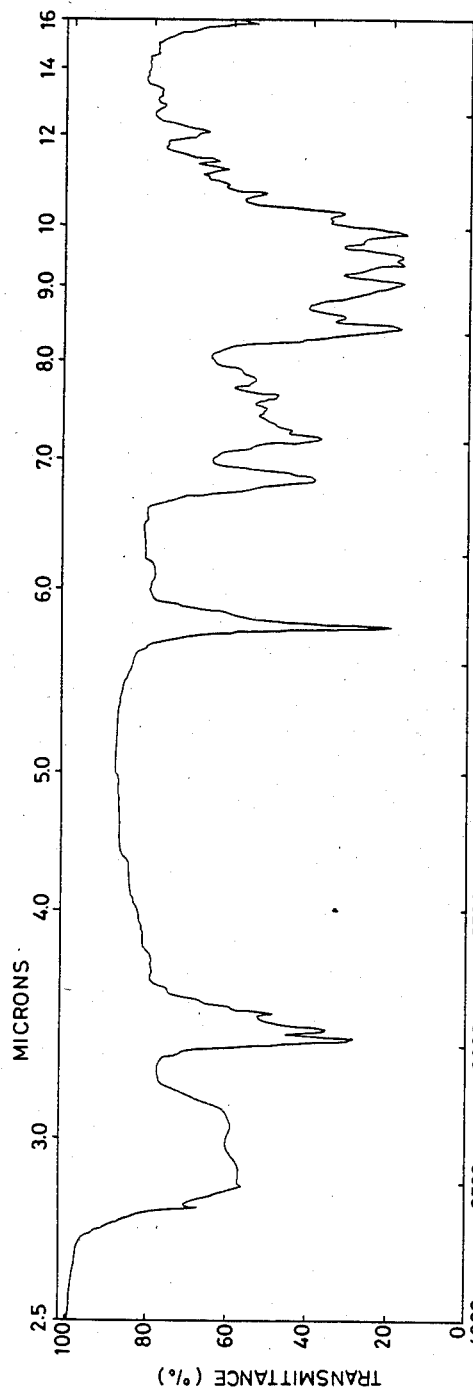

United States Patent [19]

Cappelletti et al.

[11] Patent Number: 4,560,662

[45] Date of Patent: Dec. 24, 1985

[54] *STREPTOMYCES ANTIBIOTICUS* ATCC 31771 AND PROCESS FOR OBTAINING SAME

[75] Inventors: Leonardo M. Cappelletti, Fayetteville, N.Y.; Roberto Spagnoli; Luciano Toscano, both of Milan, Italy

[73] Assignee: Pierrel S.p.A., Naples, Italy

[21] Appl. No.: 548,323

[22] Filed: Nov. 3, 1983

Related U.S. Application Data

[62] Division of Ser. No. 338,117, Jan. 8, 1982, Pat. No. 4,429,115.

[30] Foreign Application Priority Data

Jan. 9, 1981 [IT] Italy ................................ 19081 A/81

[51] Int. Cl.$^4$ ........................... C12R 1/48; C12N 1/20
[52] U.S. Cl. .................... 435/253; 435/888; 435/74; 435/75; 435/76
[58] Field of Search ................. 435/41, 74, 75, 76, 435/253, 888

[56] References Cited

U.S. PATENT DOCUMENTS

| | | | |
|---|---|---|---|
| 3,697,547 | 10/1972 | Kurath | 260/343 |
| 3,855,200 | 12/1974 | Krowicki et al. | 260/210 E |
| 3,992,264 | 11/1976 | Kierstead et al. | 435/888 |
| 4,152,424 | 5/1979 | Kierstead et al. | 435/888 |

FOREIGN PATENT DOCUMENTS 564945  1/1963  Canada ............................... 435/888

OTHER PUBLICATIONS

Bolshakova, Chemical Abstracts, vol. 95, p. 218834; 1981; No. 218830d.
*The Journal of Antibiotics* (Jul. 1976) "A New Semisynthetic Macrolide Antibiotic 3-0-Olendrosyl-5-0-Desosaminylerthronolide A Oxime."

*Primary Examiner*—Sam Rosen
*Assistant Examiner*—William J. Herald
*Attorney, Agent, or Firm*—Murray, Whisenhunt & Ferguson

[57] ABSTRACT

The fermentation of a substrate selected among erythronolide B, erythronolide A and erythronolide A oxime with a novel mutant, Streptomyces antibioticus ATCC 31771, obtained from an industrial stock for the production of oleandomycin, said novel mutant being incapable of producing the same oleandomycin, permits novel macrolide antibiotics to be produced, having not only an activity range like that of erythromycin, but characterized by a greater stability in acidic environment, whereby for the administration of the antibiotic it is no longer necessary to have recourse to esters and/or salts highly toxic for the organism.

4 Claims, 4 Drawing Figures

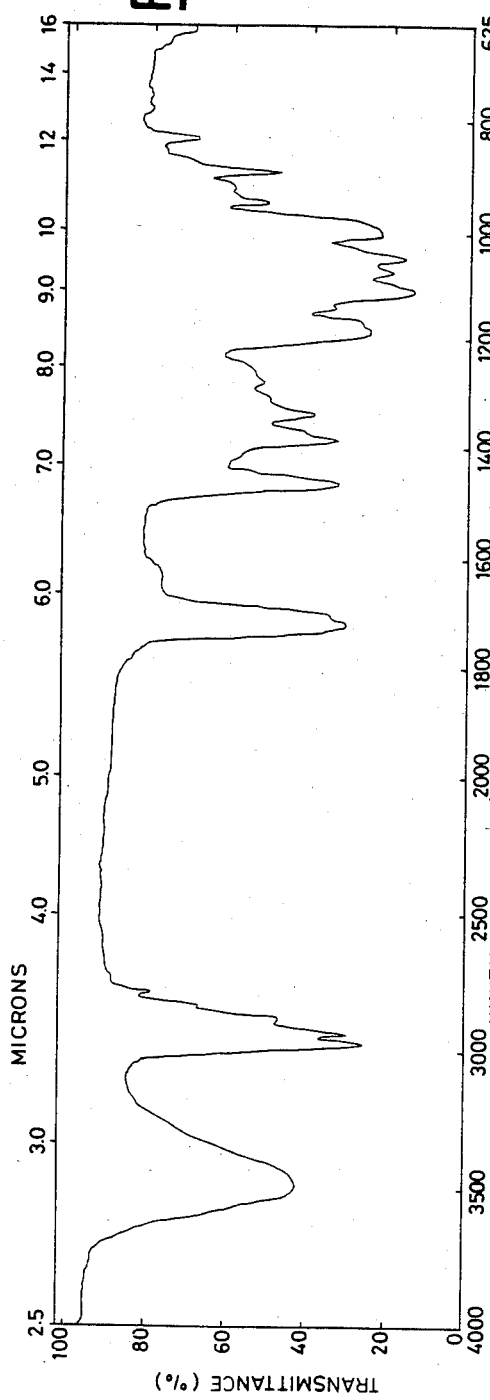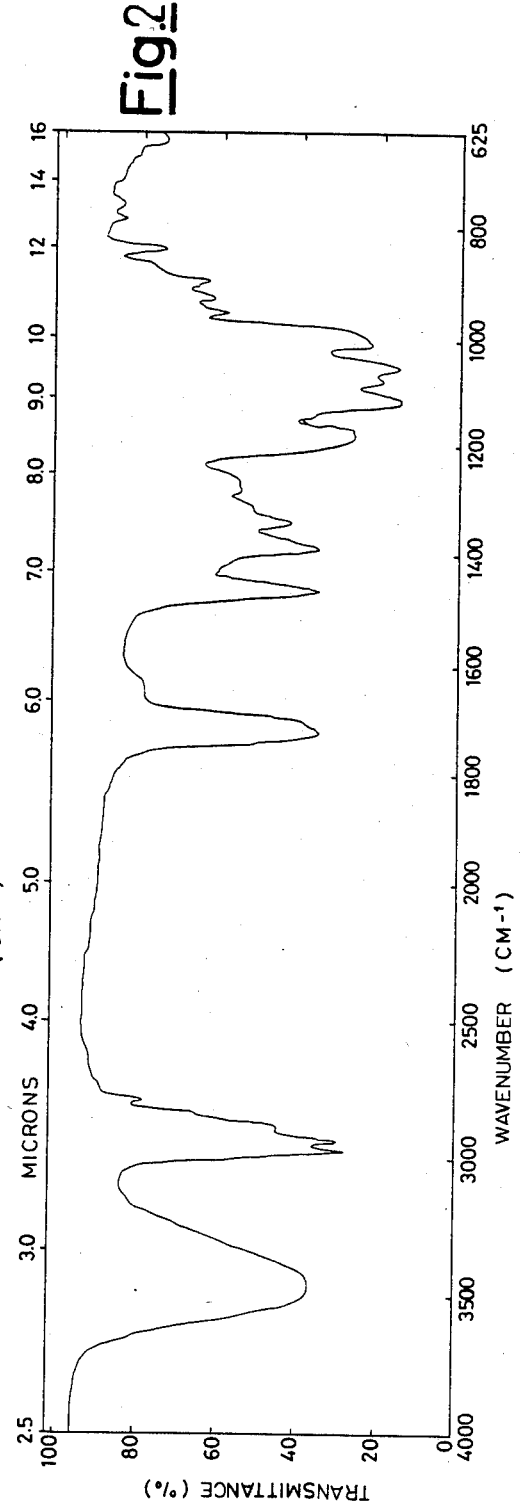

STREPTOMYCES ANTIBIOTICUS ATCC 31771 AND PROCESS FOR OBTAINING SAME

This is a division application of Ser. No. 338,117 filed Jan. 8, 1982 now U.S. Pat. No. 4,429,115.

The present invention relates to novel antibiotics of the macrolide family. More specifically the present invention relates to novel macrolide antibiotics obtained both starting from erythronolide B having the formula:

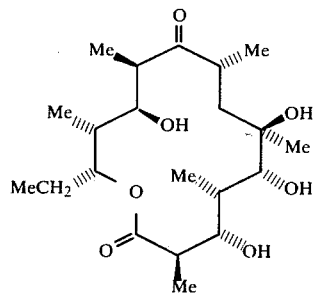

namely a natural substrate which is the biosynthetic precursor of the erythromycin A, and from semisynthetic substrates such as erythronolide A, having the formula:

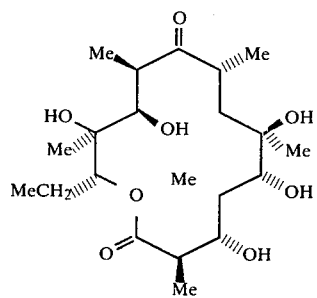

and erythronolide A oxime, having the formula

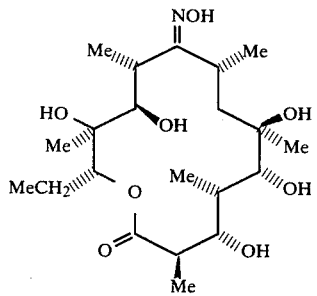

Another object of the present invention is a novel microorganism, *Streptomyces antibioticus* ATCC 31771 obtained by mutagenic treatment from *Streptomyces antibioticus* ATCC 11891, producer of oleandomycin. It is known that the *Streptomyces antibioticus* ATCC 11891, is capable of using a semisynthetic substrate (erythronolide A oxime) (LeMahieu et al, J. Antib., 1976, (7), 728), but not the aforesaid erythronolide B, which is a substrate which can be obtained by direct fermentation in relevant amounts and thus at economically feasible costs using micro-organisms producers of erythromycin and their mutants.

On the other side it is known that erythromycin is highly unstable in acidic environment, whereby the administration thereof must take place in form of esters and/or salts which, even if improve the stability, give place to well known properties of the active principle, objectionable and unfavourable from the therapeutical point of view, such as hepatic toxicity, low tolerability and others.

The oleandomycin by itself is known for its high toxicity.

The main purpose of the present invention is that of providing novel antibiotics having activity like that of the erythromycin, but devoid of the afore mentioned disadvantages of this antibiotic and particularly stable in acidic environnment and administerable without the necessity of having recourse to toxic esters and/or salts.

Another purpose of the present invention is that of providing a process for obtaining these antibiotics starting from a novel micro-organism, capable of using natural and semisynthetic substrates, particularly erythronolide B.

A further purpose of the present invention is that of providing a composition having antibiotic activity for the treatment of diseases induced by germs and bacteria sensitive to the action of erythromycin and of the like antibiotics.

These purposes are achieved by means of the novel macrolide antibiotics and the related preparation process according to the present invention which is characterized in that for the fermentation, carried out in a per se known manner, a substrate selected among erythronolide B, erythronolide A and erythronolide A oxime and, as the fermentation agent, *Streptomyces antibioticus* ATCC 31771 are used.

Another feature of the present invention resides in the preparation of the aforesaid fermentation agent, namely the *Streptomyces antibioticus* ATCC 31771 which is derived from the *Streptomyces antibioticus* ATCC11891 by mutagenic treatment with ultraviolet rays, with an emission maximum at 254 nm and at a dosage such as to kill about 99.6% of the spores, the desired micro-organism being furthermore characterized by the incapability of producing oleandomycin.

By considering in a greater detail the novel macrolide antibiotics of the present invention, they shall be hereinafter individuated on the basis of the substrate from which they are prepared and on the basis of the characteristics of chromatographic analysis (the own reference of the Applicant being indicated in brackets).

(1) 3-O-oleandrosyl-5-O-desosaminyl-(8S)-8-hydroxyerythronolide B (P 15148), having the formula:

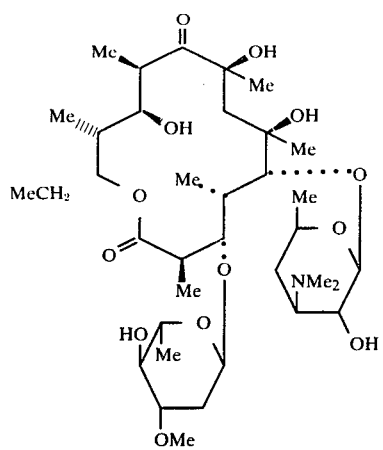

It is obtained from erythronolide B by means of the micro-organism of the present invention; at the thin layer chromatografic analysis (TLC) has $R_{st}$ of 0.8 with respect to the oleandomycin and $R_{st}$ of 0.75 with respect to the erythromycin A. By using the anisaldehyde reagent (by which the oleandomycin takes violet colour and the erythromycin A brown colour) this antibiotic takes a purple colour.

Under HPLC (high pressure liquid phase chromatography) the peak corresponding to P 15148 has a retention time with respect to erythromycin A of 0.69 and with respect to oleandomycin of 1.08.

(2) 3-O-oleandrosyl-5-O-desosaminyl-erythronolide B (P 15149), having the formula:

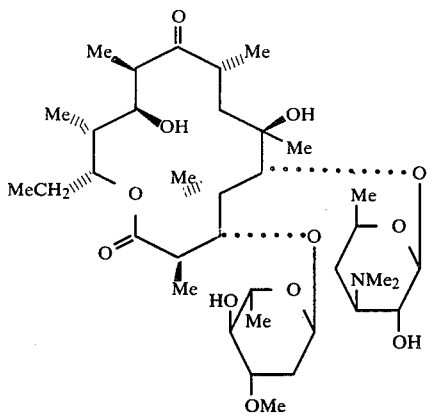

It is also obtained through fermentation of erythronolide B and has $R_{st}$ of 0.9 with respect to oleandomycin and $R_{st}$ of 0.85 with respect to erythromycin A. In the anisaldehyde test it is violet coloured. Under HPLC the peak corresponding to P 15149 has a retention time with respect to erythromycin A of 0.79 and with respect to oleandomycin of 1.22.

(3) 3-O-oleandrosyl-5-O-desosaminyl-15-hydroxyerythronolide B (P 15150), having the formula:

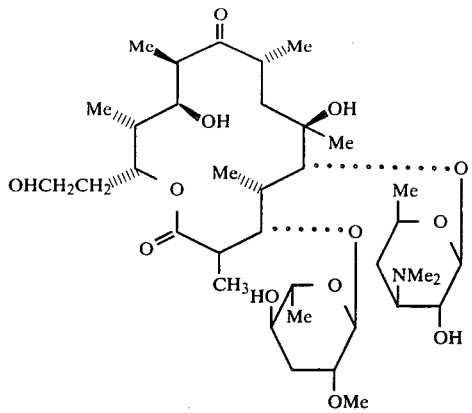

It is obtained by fermentation with *Streptomyces antibioticus* ATCC 31771 from erythronolide B as the substrate and has $R_{st}$ of 0.47 with respect to the oleandomycin and $R_{st}$ of 0.44 with respect to the erythromycin A. At the anisaldehyde test it is purple coloured. Under HPLC the peak corresponding to P 15150 has a retention time with respect to erythromycin A of 0.52 and with respect to oleandomycin of 0.80.

(4) 3-O-oleandrosyl-5-O-desosaminyl-(8S)-8,19-epoxyerythronolide B (P 15153), having

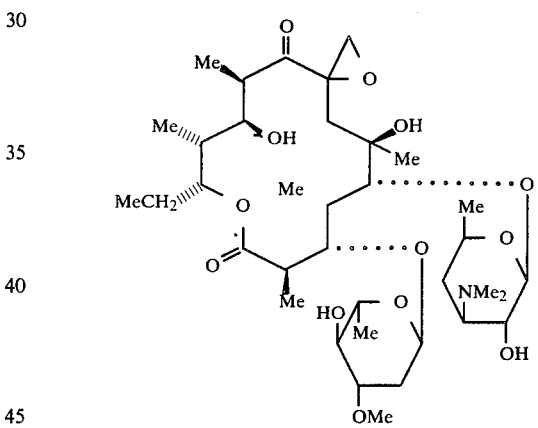

It is obtained by fermentation with the micro-organism of the invention from erythronolide B; at the thin layer chromatographic analysis (TLC) shows $R_{st}$ of 0.8 with respect to the oleandomycin and $R_{st}$ of 0.75 with respect to erythromycin A. By using the anisaldehyde reagent this antibiotic appears violet coloured.

Under HPLC the peak corresponding to P 15153 has a retention time with respect to erythromycin A of 0.64 and with respect to oleandomycin of 0.99. For the above four antibiotics, which are obtained in admixture from erythronolide B, after 100 hours of fermentation and before the isolation, the total antibiotic activity, expressed as activity of erythromycin A, is about 120-150 mcg/ml.

(5) P 15151. It is obtained from the fermentation with *Streptomyces antibioticus* ATCC 31771 of erythronolide A and has $R_{st}$ of 0.88 with respect to oleandomycin and $R_{st}$ of 0.8 with respect to erythromycin A.

From the analysis of the culture broth, after 90 hours of fermentation, there is found an antibiotic activity, expressed as activity of erythromycin A, of about 70 mcg/ml.

(6) P 15152. It is obtained from erythronolide A oxime, has Rf of 0.47 with respect to the oleandomycin and of 0.44 with respect to the erythromycin A.

From the analysis of the culture broth, after 90 hours of incubation, there is detected a total antibiotic activity of about 50 mcg/ml (expressed as activity of erythromycin A), such an activity being however referred to the mixture of P 15152 and of another antibiotic, which is concomitantly produced, which is the same already described in J. Antib. (1976), 29, 728.

Turning now to an examination of the novel macrolide antibiotics produced according to the present invention, they are all characterized by a bacteriostatic spectrum like that of erythromycin and by the stability in acidic environment, whereby their direct administration by oral route is possible, without having recourse to esters and/or salts, showing the afore mentioned disadvantages and problems. The above is confirmed by the following Table 1, wherein the MIC values are reported, indicating the bacteriostatic power, and by the Table 2, giving the stability values in acidic environment. Without having to be construed in a limiting sense, it seems plausible that the greater stability of the macrolide. antibiotics of the present invention can be attributed to the presence in the molecule of the antibiotic of the neutral sugar oleandrose (J. Antib. (1976) XXIX (7), 728).

TABLE 2

Stability in acidic environment at 25° C. of the novel antibiotics in comparison with erythromycin A

| ERYTHROMYCIN A | | | |
|---|---|---|---|
| pH | 2.0 | 3.0 | 4.0 |
| t ½ (minutes) | 2 | 6 | 120 |
| P 15148 | | | |
| pH | 2.0 | 3.0 | 4.0 |
| t ½ (hours) | 27 | >100 | >100 |
| P 15149 | | | |
| pH | 2.0 | 3.0 | 4.0 |
| t ½ (hours) | 18 | >100 | >100 |
| P 15150 | | | |
| pH | 2.0 | 3.0 | 4.0 |
| t ½ (hours) | >100 | >100 | >100 |
| P 15153 | | | |
| pH | 2.0 | 3.0 | 4.0 |
| t ½ (hours) | 65 | >100 | >100 |

Note:
t ½ represents the half life time of the antibiotics as determined by high pressure liquid phase chromatography (HPLC).

The following examples illustrate, without limiting sense, the preparation of the *Streptomyces antibioticus* ATCC 31771 and of the novel antibiotics of the invention.

EXAMPLE 1

Preparation of mutant *Streptomyces antibioticus* ATCC 31771

A suspension of spores of *Streptomyces antibioticus* ATCC 11891, producer of oleandomycin, has been subjected to mutagenic treatment with U.V. rays (emis-

TABLE 1

Bacteriostatic power in solid medium of Erythromycin A, Erythromycin B, oleandomycin, P 15149, P 15148, P 15153, P 15150 on aerobic and anaerobic bacteria, Gram positive and Gram negative minimum inhibiting concentrations expressed in mcg/ml.

| Microorganism | Product | Erythromycin A | Erythromycin B | oleandomycin | P 15149 | P 15148 | P 15153 | P 15150 |
|---|---|---|---|---|---|---|---|---|
| 1. AEROBIC | | | | | | | | |
| A. Gram positive | | | | | | | | |
| *Staphylococcus aureus* ATCC 6538 P | LRP 39 | 0.049 | 0.097 | 0.39 | 0.78 | 1.56 | 0.195 | 3.12 |
| *Staphylococcus aureus* | LRP 14°° | 0.049 | 0.195 | 0.39 | 0.78 | 1.56 | 0.195 | 3.12 |
| *Staphylococcus aureus* ATCC 14154 | LRP 78° | >25 | >25 | >25 | >25 | >25 | >25 | >25 |
| *Streptococcus faecalis* | LRP 7 | 0.097 | 0.195 | 1.56 | 0.78 | 0.78 | 0.78 | 6.25 |
| *Streptococcus faecalis sub. zymogenes* ATCC 12958 | LRP 61 | 0.195 | 0.195 | 1.56 | 0.78 | 0.78 | 0.39 | 3.12 |
| *Streptococcus pneumonieae* ATCC 6303 | LRP 35 | 0.012 | 0.024 | 0.195 | 0.097 | 0.195 | 0.049 | 0.195 |
| *Streptococcus pneumonieae* | LRP 52 | 0.012 | 0.024 | 0.195 | 0.097 | 0.195 | 0.049 | 0.195 |
| *Streptococcus pneumonieae* | LRP 53 | 0.012 | 0.024 | 0.195 | 0.097 | 0.097 | 0.024 | 0.39 |
| *Streptococcus pyogenes* ATCC 8668 | LRP 34 | 0.012 | 0.024 | 0.195 | 0.097 | 0.195 | 0.049 | 0.097 |
| *Streptococcus pyogenes* | LRP 197 | 0.012 | 0.024 | 0.195 | 0.097 | 0.195 | 0.049 | 0.097 |
| *Corynebacterium diphteriae* | LRP 24 | 0.006 | 0.012 | 0.097 | 0.049 | 0.097 | 0.024 | 0.097 |
| *Micrococcus luteus* ATCC 9341 | LRP 6 | 0.006 | 0.006 | 0.049 | 0.097 | 0.049 | 0.024 | 0.195 |
| *Micrococcus luteus* ATCC 15957 | LRP 193° | >25 | >25 | >25 | >25 | >25 | >25 | >25 |
| *Bacillus subtilis* | LRP 25 | 0.049 | 0.049 | 0.39 | 0.039 | 0.78 | 0.195 | 3.12 |
| B. Gram negative | | | | | | | | |
| *Haemophilus influenzae* ATCC 19418 | LRP 213 | 3.12 | 6.25 | >25 | 6.25 | >25 | 12.5 | >25 |
| *Neisseria Gonorrhoeae* ATCC 19424 | LRP 214 | 0.049 | 0.097 | 0.195 | 0.195 | 1.56 | 0.195 | 0.195 |
| *Escherichia coli* | LRP 50 | 6.25 | 25 | >25 | >25 | >25 | 25 | >25 |
| *Klebsiella pneumoniae* | LRP 54 | 25 | 25 | >25 | >25 | >25 | >25 | >25 |
| *Proteus vulgaris* ATCC 6380 | LRP 13 | >25 | >25 | >25 | >25 | >25 | >25 | >25 |
| *Pseudomonas aeruginosa* | LRP 9 | >25 | >25 | >25 | >25 | >25 | >25 | >25 |
| *Salmonella typhi* | LRP 8 | 12.5 | 25 | >25 | >25 | 25 | 25 | 25 |
| *Shigella sonnei* | LRP 5 | 12.5 | >25 | >25 | >25 | >25 | >25 | >25 |
| *Acholeplasma laidlawii* ATCC 23206 | LRP 204 | 0.097 | 0.097 | 6.25 | 12.5 | 6.25 | 1.56 | 6.25 |
| *Mycoplasma hominis I* ATCC 14097 | LRP 211 | >25 | >25 | >25 | >25 | >25 | >25 | >25 |
| 2. ANAEROBIC | | | | | | | | |
| *Clostridium perfrigens* ATCC 3624 | LRP 206 | 1.56 | 1.56 | 3.12 | 12.5 | 25 | 3.12 | 6.25 |
| *Bacteroides fragilis* ATCC 23745 | LRP 205 | 0.195 | 0.195 | 0.39 | 3.12 | 6.25 | 6.25 | >25 |
| *Fusobacterium necrophorum* ATCC 27852 | LRP 210 | 1.56 | 6.25 | 6.25 | >25 | >25 | 25 | >25 |

Legenda:
°Erythromicina resistant
°°Penycilline resistant sion maximum at 254 nm) at a dosage such as to kill about 99.6% of the spores (about 3000 erg/sp. cm.).

The surviving spores have been seeded on a nutrient medium and the resulting colonies have been analized looking for their uncapability of producing oleandomycin, using the method described by A. Kelner (1949) J. Bact. 57, 73.

The mutants blocked in the oleandomycin synthesis (about 2% of the surviving organisms) have been then analized with respect to their capability of recognizing and converting the substrates erythronolide B, erythronolide A and erythronolide A oxime, to novel compounds having antibiotic activity.

EXAMPLE 2

Preparation of the antibiotics
3-O-oleandrosyl-5-O-desosaminyl-(8S)-8-hydroxyerythronolide B (P 15148),
3-O-oleandrosyl-5-O-desosaminyl-erythronolide B (P 15149),
3-O-oleandrosyl-5-O-desosaminyl-(8R)-8.19-epoxy-erythronolide B (P 15153) and
3-O-oleandorsyl-5-O-desosaminyl-15-hydroxyerythronolide B (P 15150)

Method A

The mutant *Streptomyces antibioticus* ATCC 31771 is maintained on agarized culture slants of the following medium:

| | |
|---|---|
| peptone | 0.2 grams per 100 mls |
| glycerine | 0.5 grams per 100 mls |
| sugar can molasses | 0.5 grams per 100 mls |
| $K_2HPO_4$ | 0.1 grams per 100 mls |
| $MGSO_4.7H_2O$ | 0.05 grams per 100 mls |
| NaCl | 0.5 grams per 100 mls |
| $FeSO_4.7H_2O$ | 0.001 grams per 100 mls |
| $CoCl_2.6H_2O$ | 0.002 grams per 100 mls |
| agar | 2.0 grams per 100 mls |
| distilled water | to volume |
| pH | corrected to 7.0 |

With a spore amount taken from one slant a 500 ml Erlenmeyer flask is seeded, containing 50 ml of cultivation medium having the following composition:

| | |
|---|---|
| dextrose | 1.5 grams per 100 mls |
| soy bean meal | 3.0 grams per 100 mls |
| yeast autolysate | 0.1 grams per 100 mls |
| $MgSO_4.7H_2O$ | 0.1 grams per 100 mls |
| calcium carbonate | 1.0 grams per 100 mls |
| soy bean oil | 0.6 grams per 100 mls |
| distilled water | to volume |

The flask is incubated at 28° on a rotary shaker at 220 rpm for 24 hours. After this time, a 10 liter glass fermentor containing 5 liters of the aforesaid medium is seeded with 15 mls of this culture. The fermentor is incubated at 28° C., under 800 rpm stirring and with an air flow of 0.6 v/v/min. for 16 hours.

At the end of this period, 3.5 liters of the above culture are used for seeding a 200 liter steel fermentor containing 100 liters of the following medium:

| | |
|---|---|
| dextrose | 5.0 grams per 100 mls |
| soy bean meal | 2.0 grams per 100 mls |
| dried baker yeast | 0.4 grams per 100 mls |
| corn meal | 1.6 grams per 100 mls |
| calcium carbonate | 3.0 grams per 100 mls |
| NaCl | 0.3 grams per 100 mls |
| fat oil | 1.0 grams per 100 mls |
| tap water | to volume |

The incubation is carried out at 28° C. with 250 rpm stirring and an aeration of 1 v/v/min.

After 32 hour growth the culture is added with 75 g of erythronolide B and the incubation is continued for further 68 hours.

At the end of this time a sample of the culture broth is filtered and extracted at pH 8.5 with an equal volume of $CH_2Cl_2$.

The extract is analyzed by TLC on silica gel plates developed for 2 hours with the system $CH_2Cl_2$:95% methanol:conc. $NH_4OH$(90:10:1).

By this plate a bioautography is effected against Micrococcus luteus (Sarcina lutea) ATCC 9341 or alternatively the plates can be sprayed with an anisaldehyde reagent (0.5% v/v of anisaldehyde in a mixture of methanol:glacial acetic acid:conc. sulfuric acid, (85:10:5)) and heated to 120° C. for 5 minutes.

Under the above fermentation conditions and parallel to the use of the erythronolide B, four novel substances having antibiotic activity and indicated by the references P 15148, P 15149, P 15150 and P 15153 are produced. Under TLC these substances show $R_{sl}$ values of 0.8, 0.9, 0.47 and 0.8 with respect to the oleandomycin. With respect to erythromycin these $R_{sl}$ values are 0.75, 0.85, 0.44 and 0.75.

By using the anisaldehyde reagent, the products P 15148, P 15150 and P 15153 appear purple coloured, whereas P 15149 is violet coloured (the oleandomycin is violet, whereas the erythromycin is brown).

A sample of the organic extract is also controlled under HPLC.

To this end it is evaporated to dryness, taken with acetonitrile and injected in column (RP810 $\mu$m 25 cm; mobile phase 0.01M pH 7 phosphate buffer and acetonitrile (36:64); flow 2 mls/min; column temperature 40° C.).

For the novel substances P 15148, P 15149, P 15150 and P 15153 peaks are detected with retention times with respect to erythromycin A of 0.69, 0.79, 0.52 and 0.64 and with respect to oleandomycin of 1.08, 1.22, 0.80 and 0.99.

After 100 hours of fermentation the total antibiotic activity, expressed as activity of erythromycin A, is about 120 to 150 mcg/ml.

The stirring is reduced to a minimum by stopping the air feeding and the temperature is lowered to 15° C.

Method B

A fermenting culture of *Streptomyces erythreus* NRRL 2338 is prepared according to the conditions described in the German open application (OS) 1900647 of Aug. 13, 1970.

By adding 4% v/v n-propanol, after 144 hours of fermentation, in the culture broth about 500 mcg/ml of erythronolide B and traces of erythromycin (less than 20 mcg/ml) are obtained.

At this time the culture is centrifuged and the clear supernatant is sterilized by filtration.

A vegetating culture of *Streptomyces antibioticus* ATCC 31771 is prepared according to the procedure described in the method A.

A second growing passage is carried out under the same conditions by seeding with 1 ml of vegetating culture a second 500 ml Erlenmeyer flask containing 50 mls of the cultivation medium of method A.

With 1.0 mls of second growth culture a 500 ml Erlenmeyer flask is seeded, containing 30 mls of the following culture medium:

| | |
|---|---|
| dextrose | 5.0 grams per 100 mls |
| soy bean meal | 2.0 grams per 100 mls |
| baker yeast | 0.2 grams per 100 mls |
| maize meal | 0.3 grams per 100 mls |
| calcium carbonate | 2.0 grams per 100 mls |
| tap water | to volume |

The flask is incubated at 28° C. on rotary shaker at 250 rpm. After 32 hours of incubation the flask is added with 10 mls of the afore described clear supernatant and the incubation is continued for further 64 hours.

The culture is analized according to the procedure described in the method A. A total antibiotic activity (expressed as activity of erythromycin A) of about 30 mcg/ml is obtained; by HPCL the presence of the four novel antibiotics P 15148, P 15149, P 15150 and P 15153 as well as traces of erythromycin A are detected.

In the control flasks, for which no addition of the filtrate containing erythronolide B took place, the antibiotic activity is absent.

EXAMPLE 3

Purification of the antibiotics
3-O-oleandrosyl-5-O-desosaminyl-(8S)-8-hydroxyerythronolide B (P 15148),
3-O-oleandrosyl-5-O-desosaminylerythronolide B (P 15149),
3-O-oleandrosyl-5-O-desosaminyl-(8R)-8,19-epoxyerythronolide B (P 15153) and
3-O-oleandrosyl-5-O-15-hydroxyerythronolide B (P 15150)

To the final fermentation mixture, repeated in the example 2 (method A), there are added under stirring 30 liters of a 10% w/v $ZnSO_4$ solution and 30 liters of a 2% w/v NaOH water solution.

After addition of a filtration aid, the solid content is removed by filtration through a rotary filter under vacuum after continuous washing of the solid on the filter cake. The washed solids are disposed and, at the end of the filtration, 150 liters of clear filtrate are recovered.

The filtrate is then salted with a suitable salt, such as NaCl, $Na_2SO_4$, $(NH_4)_2SO_4$ and the like added in an amount of 15 to 25% w/v in order to facilitate the subsequent extraction with a suitable solvent not miscible with water. The pH of the filtrate is corrected to between 5.4 and 6.2 by means of diluted acids, such as for instance phosphoric or acetic acid.

By this operation the inactive solids are precipitated and then removed by filtration.

A suitable solvent not miscible with water such as butyl acetate, chloroform, methylisobutylketone, methylene chloride or dichloroethane is contacted, by means of a continuously operating centrifugal extractor, with the clear filtrate, in a ratio of between 20 and 50% v/v.

The operation is repeated twice and the organic phases are combined.

The combined organic phases prevailingly contain P 15149. In the aqueous phase P 15148, P 15150, P 15153 and residual P 15149, not completely extracted from the organic phase, are present.

The organic phase (about 100 liters) is distilled under vacuum at low temperature to a volume of about 10 liters.

Under vigorous stirring there are added 3 liters of $10^{-4}$M acetate buffer at a pH of about 4.0 and the phases are then separated.

The operation is repeated three times and at the end all the P 15149 is present in the acqueous phase; the solvent, containing much impurities, is disposed.

The combined aqueous phases are brought to a pH of about 8.0 with diluted NaOH and then extracted three times with 3 liter fractions of an organic solvent such as methylethylketone or butyl acetate. The water phase is disposed and the organic phases are combined and dried onto anhydrous $Na_2SO_4$.

The dried solution is distilled under vacuum at low temperature to a volume of 500 mls.

To 5 liters of a non polar solvent, such as hexane or petroleum ether heated to about 40° C. there are added, under stirring, 500 mls of the concentrated solution; the addition is completed over about 1 hour.

At the end of the addition the heating is stopped and the mixture is cooled slowly to +5° C.

After about 2 hour standing at that temperature, the precipitation of P 15149 which already began at about 18° C. is completed.

The white and fluffly precipitate is filtered, washed with solvent and dried, giving place to 4.2 g of P 15149 which at HPLC analysis show a purity of 85%.

In order to obtain n an analitically pure sample it is necessary to further purify the solid by means of column chromatography on silica gel according to the method indicated by N. L. Oleinick, J. Biol. Chem., Vol. 244, N. 3, pag 727 (1969).

The 25-80 fractions, containing 3-O-oleandrosyl-5-O-deoxaminyl-erythronolide B (P 15149) are combined, evaporated to dryness under vacuum at 50° C., and crystallized from acetone-n-hexane, giving 1.835 g of P 15149 having the following characteristics:

m.p.: 128°–131° C.

$[\alpha]_D^{20} -68.2°$ (C=1 in methanol); UV (methanol) 290 nm ($\epsilon$ 59.8); IR (KBr) 3490, 1720, 1700 (shoulder), 1460, 1380, 1335, 1275, 1250 (shoulder), 1180, 1160, 1140, 1105, 1075, 1050, 1000, 945, 920, 890, 830 cm$^{-1}$ (FIG. 1).

The analysis for $C_{36}H_{65}NO_{12}$ gave the following values: calculated (%): C 61.43; H 9.30; N 1.99. found (%): C 61.34; H 9.38; N 2.05.

The aqueous phases containing P 15148, P 15150, P 15153 and P 15149 (not completely extracted) are made alkaline with diluted NaOH, extracted several times with an equal volume of $CH_2Cl_2$. Before each extraction the pH of the aqueous phase is brought again to 9.

By TLC and HPLC control it is possible to individuate the extracts containing only the antibiotic P 15150 (more soluble than the others in water phase) and the extracts still containing P 15148, P 15149, P 15150 and P 15153 together.

The organic phases containing only P 15150 are combined and evaporated under vacuum at 50° C. to dryness, giving 3.4 g of P 15150 with the following chemical and physical characteristics:

$[\alpha]_D^{20} -55°$ (C=1 in methanol); UV (methanol) 288 nm ($\epsilon$42);

IR (KBr) 3460, 1715, 1700 (shoulder), 1455, 1375, 1330, 1300, 1270, 1255, 1240, 1170, 1105, 1070, 1045, 1000, 990, 980, 940, 915, 885, 825 cm$^{-1}$ (FIG. 2).

The corresponding hydrochloride has melting point 160°–163° C. (acetone).

The analysis for $C_{36}H_{65}NO_{13}\cdot HCl$ gave the following results: calculated (%): C 57.17; N 8.80; N 1.85; Cl 4.69. found (%): C 56.92; H 8.77; N 1.91; Cl 4.59.

The other organic phases, still containing P 15150 and the remaining antibiotics are evaporated to dryness under vacuum at 50° C. and the obtained residue is purified in a silica gel column according to the aforesaid method of N. L. Oleinick.

By carrying out the elution with the solvent indicated in this method fractions are collected containing only P 15149 (fractions 52 to 110), P 15148 (fractions 130 to 185), P 15153 (fractions 260 to 450). When from the TLC and HPLC control it appears that the eluted fractions no longer contain P 15153, the elution solvent is changed. By eluting with isopropyl alcohol-acetone (1:1.5) the fractions containing only the antibiotic P 15150 are collected.

The fractions 52 to 110, combined and evaporated to dryness under vacuum at 50° C. gave 0.425 g of 3-O-oleandrosyl-5-O-desosaminyl-erythronolide B (P 15149), which after crystallization from acetone n-hexane shows chemical and physical characteristic equal to those reported for the P 15149 previously isolated.

The fractions 130 to 185, combined and evaporated to dryness under vacuum at 50° C., gave 3.2 g of 3-O-oleandrosyl-5-O-desosaminyl-(8S)-8-hydroxy-erythronolide B (P 15148), after crystallization from acetone, characterized by:

m.p. 204°-206° C.

$[\alpha]_D^{20}$ —48.35 (C=1 in methanol); UV (methanol) 280 nm ($\epsilon$ 39.2) IR (KBR) 3590, 3520, 3440 (broad), 3280 (broad), 1725, 1455, 1380, 1365, 1305, 1280, 1270, 1260, 1175, 1155, 1095, 1060, 1050, 1020, 1005, 970, 935, 915, 885, 875, 820 cm$^{-1}$ (FIG. 3).

The analysis for $C_{36}H_{65}NO_{13}$ gave the following values: calculated (%): C 60.06; H 9.10; N 1.94; found (%): C 60.12; H 8.93; N 1.92.

The fractions 260 to 450, combined and evaporated to dryness under vacuum at 50° C., gave 10.3 g of 3-O-oleandrosyl-5-O-desosaminyl-(8S)-8,19-epoxy-erythronolide B (P 15153), after crystallization from acetone/n-hexane, with the following chemical and physical characteristics:

m.p. 125°-130° C.

$[\alpha]_D^{20}$ —27.7° (C=1 in methanol); UV (methanol) 294 nm (32.7)

Figure 4:
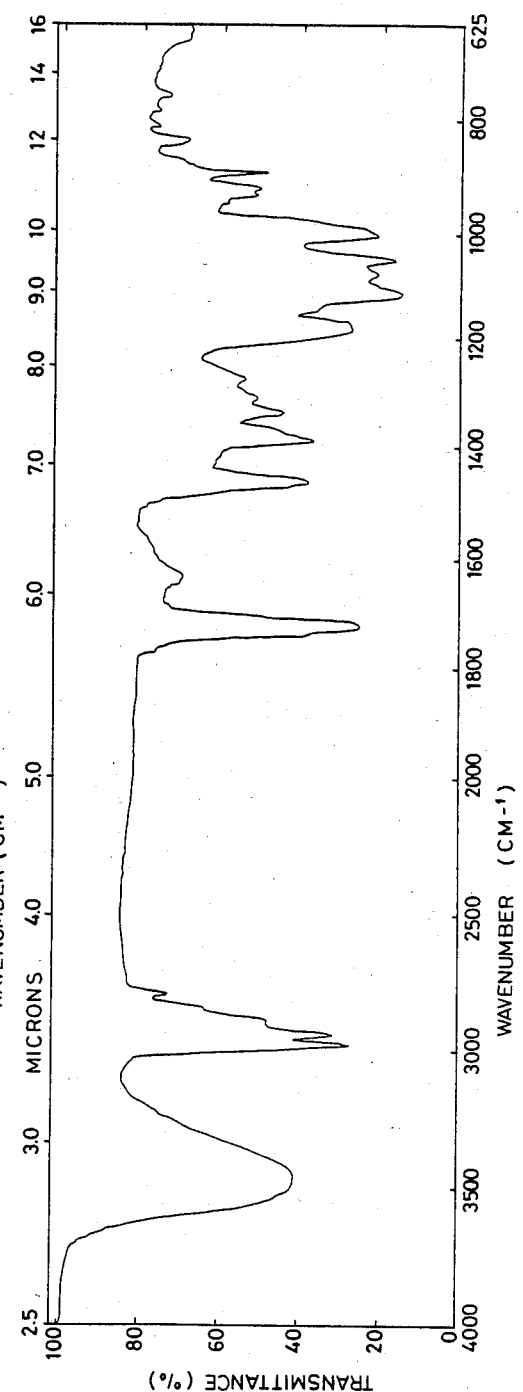

IR (KBr) 3485, 1720, 1460, 1380, 1330, 1305, 1270, 1170, 1140, 1110, 1075, 1050, 1000, 930, 920, 890, 830 cm$^{-1}$ (FIG. 4).

The analysis for $C_{36}H_{63}NO_{13}$ gave the following values: calculated (%): C 60.23; H 8.85; N 1.95. found (%): C 60.12; H 8.75; N 1.79.

By evaporation under vacuum of the fractions collected with isopropyl alcohol acetone (1:1.5) and subsequent crystallization from acetone/n-hexane, 15.4 g of P 15150 are obtained with the same properties previously indicated.

EXAMPLE 4

Preparation of the antibiotic P 15151

To a fermenting culture of *Streptomyces antibioticus* ATCC 31771 prepared in a flask according to the procedure described in the example 2, there are added, after 30 hours of incubation, 15 mg of erythronolide A prepared starting from erythromycin A according to the method described in J. Med. Chem. (1974), 17, 953.

After further 60 hours of incubation, the culture broth is analyzed as described in the example 2 and an antibiotic activity of about 70 mcg/ml (expressed as activity of erythromycin A) is found.

By TLC analysis a novel active substance, P 15151, is found, having Rf 0.8 with respect to the erythromycin A and 0.88 with respect to the oleandomycin. This compound is furthermore different from the antibiotics P 15148, P 15149, P 15150 and P 15153.

EXAMPLE 5

Preparation of the antibiotic P 15152

To a flask containing a culture of *Streptomyces antibioticus* ATCC 31771, prepared according to the procedure described in the example 4, there are added, after 30 hours of incubation, 15 mg of erythronolide A oxime, chemically prepared according to the method described in J. Med. Chem. (1974), 17, 953.

After further 60 hours of incubation, the culture broth is analized as described in the example 2 and a total antibiotic activity of about 50 mcg/ml (expressed as activity of erythromycin A) is revealed.

By TLC analysis there are found two active substances, one of which is the same described in J. Antib. (1976), 29, 728, (Rf 0.73 with respect to the oleandomycin), whereas the second one is novel and is indicated by the reference P 15152, having Rf 0.47 with respect to the oleandomycin and 0.44 with respect to erythromycin A. It is to be pointed out that, within the scope of the present invention, there are contemplated also the other possible uses of the *Streptomyces antibioticus* ATCC 31771 as regards the introduction in the moleule of precursors, either novel or already known, of macrolide antibiotics, the oleandrose meant as an agent giving stability in acidic environment and thus promoting the administration by oral route.

We claim:

1. A biologically pure culture of *S. antibioticus* ATCC 31771.

2. A process for the preparation of *S. antibioticus* ATCC 31771, comprising the steps of:
   (a) subjecting spores of a stock of *S. antibioticus* producer of oleandomycin to a mutagenic radiation treatment with U.V. rays at a dosage such as to kill not less than 99 percent of the spores;
   (b) culturing the residual spores and selecting colonies on the basis of their incapacity to produce oleandomycin and on the basis of the capacity of recognizing and converting substrates selected from the class consisting of erythronolide B, erythronolide A and erythronolide A oxime; and
   (c) isolating said *S. antibioticus* ATCC 31771.

3. A process according to claim 2, wherein said stock undergoing said mutagenic treatment is *S. antibioticus* ATCC 11891.

4. A process according to claim 2, wherein said radiation is carried out with a maximum of emission of said U.V. rays at 254 nm and with a dosage of about 3000 erg/sq.cm.

* * * * *